(12) United States Patent
Bryukhovetskiy et al.

(10) Patent No.: US 9,750,848 B2
(45) Date of Patent: Sep. 5, 2017

(54) METHOD OF PREPARING AN IMPLANTABLE NEUROENDOPROSTHETIC SYSTEM

(71) Applicants: Andrey S. Bryukhovetskiy, Moscow (RU); Viktor I. Sevastianov, Moscow (RU)

(72) Inventors: Andrey S. Bryukhovetskiy, Moscow (RU); Viktor I. Sevastianov, Moscow (RU)

( * ) Notice: Subject to any disclaimer, the term of this patent is extended or adjusted under 35 U.S.C. 154(b) by 202 days.

(21) Appl. No.: 14/748,183

(22) Filed: Jun. 23, 2015

(65) Prior Publication Data

US 2015/0290360 A1 Oct. 15, 2015

Related U.S. Application Data

(63) Continuation-in-part of application No. 13/121,069, filed as application No. PCT/RU2009/000067 on Feb. 13, 2009, now abandoned.

(30) Foreign Application Priority Data

Sep. 25, 2008 (RU) ................ 2008138161

(51) Int. Cl.
*A61L 27/38* (2006.01)
*A61K 9/70* (2006.01)
*A61K 35/30* (2015.01)
*A61K 35/44* (2015.01)
*A61L 27/24* (2006.01)

(52) U.S. Cl.
CPC .......... *A61L 27/3878* (2013.01); *A61K 35/30* (2013.01); *A61K 35/44* (2013.01); *A61L 27/24* (2013.01); *A61L 27/383* (2013.01); *A61L 27/3834* (2013.01); *A61L 27/3886* (2013.01); *A61L 2430/32* (2013.01)

(58) Field of Classification Search
CPC .................. A61L 2430/32; A61L 27/3878
See application file for complete search history.

(56) References Cited

PUBLICATIONS

Sykoyá et al (Cellular and Molecular Neurobiology. 2006; 26(7-8): 1113-1129).*
Ao et al (Medical Hypotheses. 2007: 69: 1234-1237).*
Möllers et al. (Tissue Engineering: Part A. online Aug. 26, 2008; 15(3): 461-472).*
Stanness et al (Neuropharmacology and Neurotoxicology. 1999; 10(18): 3725-3731).*
Gerecht-Nir et al. (Biotechnology and Bioengineering. 2004; 88(3): 313-320).*

* cited by examiner

*Primary Examiner* — Scott Long
(74) *Attorney, Agent, or Firm* — Patentagar PLLC; Alexander Rabinovich

(57) ABSTRACT

A method of making an implantable neuroendoprosthetic system for transubstantiation of defects of brain, spinal cord and vegetative nervous system in a mammal in reconstructive neurosurgical operations provides a heterogeneous collagen-containing matrix for implantation, a cell preparation of autologous cells of a patient, and the cell preparation is perfused into said matrix to make an elastic cell-biopolymer biologically active mass. The cell preparation comprises placed in a NaCl solution at least one type of cells from a group comprising neural stem cells (NSC), neuroglial ensheathing cells (NGEC), endothelial cells with CD34+ marker (EC), and purified mononuclears (MN). The mass can be additionally subjected to electromagnetic radiation at 1-10 GHz before implanting.

9 Claims, 1 Drawing Sheet

METHOD OF PREPARING AN IMPLANTABLE NEUROENDOPROSTHETIC SYSTEM

CROSS-REFERENCE TO RELATED APPLICATIONS

This application is a continuation-in-part application of the U.S. application Ser. No. 13/121,069 filed Mar. 25, 2011, which is a U.S. National phase application of the International application WO 2010/036141A1 (PCT/RU2009/000067) filed Feb. 13, 2009, and claims priority to application 2008138161 filed on Sep. 25, 2008, in the Russian Federation, all the three applications being hereby incorporated by reference in their entirety.

BACKGROUND OF THE INVENTION

1. Field of the Invention

The invention relates to the field of neurosurgery and tissue engineering of organs and can be applied for transubstantiation of defective neural tissue of the brain and spinal cord in reconstructive and repairing treatment of consequences of traumatic damages and ischemic injuries, as well as for surgery on central nervous system (CNS) and vegetative nervous system (VNS) of a mammal, for example a human. (A list of abbreviations used in the ensuing disclosure is placed in the end of the disclosure.)

2. Description of Related Art

Till the end of the 20$^{th}$ century, prosthetic repair of nervous tissue defects was considered impossible and almost unsolvable that can be explained by the dogmatic understanding by brain researchers, neurologists and neurosurgeons of limited restoration capacities of the nervous tissue, as well as by dogmatic notion established in 1801 by Santiago Ramon-y-Cajal stating that neural cells were inherently unable to regenerate after the injury. However, the last decade of the 20$^{th}$ century has considerably changed the approach by accumulation of new scientific evidence of regenerative potential of CNS, reparative properties of neural stem cells (NSC) and conclusive proofs of restoration opportunities of the axons of injured neurons.

Known in the art is a preparation of hematopoietic stem cells (HSC), including autologous HSC which are obtained from a patient peripheral blood enriched with cells containing a CD34 antigen in the final concentration of (40 to 100)·$10^6$ cells/ml. A therapeutic treatment of a brain and spinal cord (SC) traumatic disease is performed by an intrathecal or intraventricular administration of the cell preparation to a patient (RU 2283119 C1, A61K35/14, 2006). However, the preparation consisting of solely HSC appeared insufficiently effective in the therapy of brain and SC nervous tissue defects.

Known is a biopolymer prosthesis <<NeuroGel>>™ to fill defects of nervous tissue (S. Woerly, V. D. Doan, F. Evans-Martin, C. G. Paramore, J. D. Peduzzi, "Spinal cord reconstruction using NeuroGel™ implants and functional recovery after chronic injury", *J. of Neuroscience Res.* 2001. Vol. 66, pp. 1187-1197). The research proved a possibility of the growth of the injured axons through a biopolymer composition in a mammal SC and the restoration of lost brain functions, while stem cells provide favorable conditions for axon regeneration. However, application of the <<NeuroGel>>™ prosthesis proved inefficient in the treatment of brain and SC defects. Moreover, the <<NeuroGel>>™ composition contains agents, prohibited to be used in humans.

Also known in the art is a multipurpose heterogeneous collagen matrix for implantation, including an elastic mass prepared of two collagen sources, one being the tissue of vertebrate animal of one class, and the other being the tissue of other class of animals. The matrix consists of two phases: a solid phase represented by microspheres of a mammal tissue collagen and a liquid one represented by a denatured bird tissue collagen. This heterogeneous collagen-containing matrix was proposed for restoration of injuries of soft tissues and organs by means of implantation (RU 2249462 C1, A61K38/39, 2005). Using this collagen matrix for the implantation into a defect of nervous tissue failed to activate in full a regenerative potential of the artificial implant due to big size of microspheres (300 to 400 μm) and their hardness that led to a mechanical damage and death of transplanted stem cells.

BRIEF SUMMARY OF THE INVENTION

An object of the present invention is to provide a method of preparing (making) a replaceable-by-tissue artificial cell-biopolymer neuroendoprosthetic system (ACBP NEPS) for surgical plasty of nervous tissue defects of brain and SC, that would stimulate the regeneration and growth of damaged axons of neural cells, as well as to provide the system the method results in, and a method of reconstructive neurosurgical operation for the transubstantiation of the defects of brain and/or SC and/or a VNS in a mammal with the use of the system prepared using the above-identified method of preparing. Meant in this disclosure by transubstantiation is a replacement or substitution of one kind of tissue for another (The Free Medical Dictionary—http://medical.dictionary.thefreedictionary.com/transubstantiation).

The above object is reached, according to the present invention, by providing a heterogeneous collagen-containing matrix, providing a cell preparation of autologous cells of a patient and by perfusing the preparation into the matrix, thus creating an implantable neuroendoprosthetic system in the form of an elastic cell-biopolymer biologically active mass that can be used for the transubstantiation of defects of a brain, spinal cord and vegetative nervous system in a mammal in reconstructive neurosurgical operations.

More specifically, said cell preparation used for the implementation of the proposed method comprises placed in a NaCl solution at least one type of cells from a group comprising neural stem cells (NSC), neuroglial ensheathing cells (NGEC), endothelial cells with CD34+ marker (EC), and purified mononuclears (MN), said cells being in the following ratios (in parts according to numbers of the cells): 0.8 to 1.2 of NSC; 1.6 to 2.4 of NGEC; 4 to 6 of EC; 4000 to 6000 of MN. Preferably, 0.5 to 1.3% solution of NaCl is used. As the heterogeneous collagen matrix, a composition of a heterogeneous implantable Sphero®GEL is preferably used.

The cell preparation can further comprise stimulators of cell regeneration, nerve growth factors and vascular growth factors. The most appropriate, efficient and safe (in consideration of swelling ratio of the Sphero®GEL matrix) is the ACBP NEPS in which numbers of said cells contained in 0.5 to 1 ml of 0.9% NaCl solution per 1 ml of said heterogeneous collagen-containing matrix are as follows: $10^6$ of NSC; $2·10^6$ of NGEC; $5·10^6$ of EC; $5·10^9$ of MN and which also comprises 0.1 to 0.2 ml of a conventional solution of a cell regeneration stimulator (methyluracil, leucogen, ATP, pentoxyl, etc.).

Preferably, the perfusion is performed by centrifugation. The centrifugation is carried out within 1.5 to 2.5 minutes at 1,500 to 2,500 revolutions per minute. The cell preparation is prepared from cryopreserved cell products that, immediately before the production of said implantable neuroendoprosthetic system, are defrosted at a water bath at 37 to 40° C. and then washed at least twice in a physiological NaCl solution.

In more detail, the cell preparation comprises, in a NaCl solution, neural stem cells (NSC), neuroglial ensheathing cells (NGEC), endothelial cells with CD34+ marker (EC) and purified mononuclears (MN). A composition of a heterogeneous implantable gel Sphero®GEL, is preferably used as said heterogeneous collagen-containing matrix. A source of the NSC and the NGEC is principally olfactory sheath of the nose of a patient, and a source of the EC and the MN is either a bone marrow of the patient or a leukoconcentrate of mobilized autologous stem cells of the patient; wherein the leukoconcentrate is obtained during separation of the patient's peripheral blood after the patient was stimulated with a granulocyte colony-stimulating factor. Added into the cell preparation can be stimulators of tissue regeneration, nerve growth factors and vascular growth factors. The method of the ACBP NEPS production of the present invention is carried out in sterile conditions either directly in an operation room (ex tempore), or in a culture laboratory (with a period of implantation of up to 6 hours).

The neuroendoprosthetic system is implanted by placing the same into a defect akin to "filling" and by filling a whole volume of a cyst or a lesion of the brain and/or spinal cord by the system. After the neuroendoprosthetic system has been placed into the defect, the system is covered with an autologous muscle fascia or an artificial dura mater and/or a biodegradable synthetic polymer coat to reduce a contact of the neuroendoprosthetic system with cerebrospinal fluid (CSF) of the patient. An implantable biopolymer membrane ElastoPOB® is preferably used as said biodegradable synthetic polymer coat. In case of a complete anatomical break-up (neurotmesis) of the spinal cord, the neuroendoprosthetic system is implanted by; forming a conduit from an artificial arterial graft and the neuroendoprosthetic system; filling, at least partially, the graft by the neuroendoprosthetic system, further placing the conduit in the diastasis area (gap) between the ends of the injured spinal cord, and then suturing pia mater of distal and proximal ends of the injured spinal cord to the conduit walls. The length of the artificial arterial graft is equal to the length of said gap, and the width of the graft is equal to the diameter of the spinal cord in the lesion site. Upon intramedullar or intracerebral implantation, the neuroendoprosthetic system is isolated from a direct impact of CSF.

The implantable biopolymer membrane ElastoPOB® is produced by ZAO Biomir-Service (Moscow) according to technical standards TU 9398-002-54969743-2006, registration certificate No. FC 0103200615581-06 of Dec. 28, 2006,

BRIEF DESCRIPTION OF DRAWINGS

Efficiency of the ACBP NEPS of the present invention is illustrated by the following figures.

DESCRIPTION OF PREFERRED EMBODIMENTS

Figure 1:
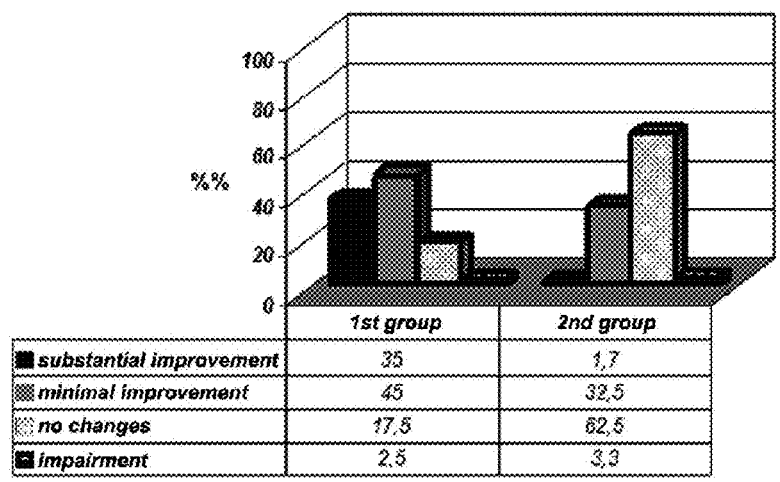
FIG. 1, in Which a diagram is shown demonstrating efficiency of the treatment of patients with a traumatic brain and spinal cord injury by the method of the present invention and a conventional method.

The consistency and structure of the proposed ACBP NEPS provide adequate modeling of a neuroimplant in the damaged regions of brain and spinal cord and local stimulation of regeneration processes in the brain and spinal cord damage sites. The use of only autologous cells preparations in the ACBP NEPS averts problems of histocompatibility and immune conflict, as well as the need of using immunosuppressants. Ethic, legal and moral limitations are also absent as the treatment involves only autologous cells of the patient. The risk of infectious and viral contamination is excluded, as well as the risk of prion infection possible in case of application of xenogeneic materials. The exact amount of the applied ACBP NEPS is defined depending on volume, character and location of a brain/spinal cord damage.

The creation of the ACBP NEPS was based on the development and production of a polymer matrix that would meet specific demands of "bridging" the gap between the damaged regions of brain/spinal cord, provide support and nutrition for the cell preparations, function as an orienting vector for the axons of the injured autoneurons and neuroglial cells, help stimulate regeneration of the injured axons, and, contributing to their growth through the defect region of the nervous tissue, prevent the process of sprouting from occurring. The proposed matrix should meet safety criteria and biodegrade into safe components within a preset time span (8 to 12 months) being replaced by restored nervous tissue.

The preferable matrix to be used in the ACBP NEPS used for the proposed method is the composition of the heterogeneous implantable gel traded as Sphero®GEL (Russian trademark registration No. 269774) and produced by ZAO Biomir-Service (Moscow) according to technical standards TU 9398-001-54969743-2006 of Dec. 26, 2006, registration certificate No. FC 01032006/5580-06 of Dec. 28, 2006.

The Sphero®GEL matrix comprises micro particles of cross-linked collagen of type VII obtained from farm animals, which micro particles are suspended in elastic homogeneous gel. The matrix is not a natural product. It is a unique complex of peptides (30 to 50 mg/g), uronic acids (0.8 to 1.2 mg/g) and hexosamines (2.0 to 3.0 mg/g). Amino-acid composition of the matrix is identical to that in the collagen, but its hexosamine content is twice as much, and uronic acids content is 15 times higher, than that in the collagen. The Sphero®GEL matrix is stable for long-term storage and not susceptible to syneresis (expulsion of a liquid phase). Consequently, it does not interfuse with water and hydrophobic liquids. At 37° C., the gel turns into liquid interfusing with water and the micro particles of the cross-linked collagen in all ratios. The size of the gel micro particles can be varied from 30 to 300 μm. The swelling capacity of the Sphero®GEL matrix is no less than 87%, pH=4.8 to 7.2. The average time of bio resorption in a body varies from several weeks to 9 months depending on the site of implantation and the size of the micro particles. High biological compatibility and stimulating properties of the biopolymer implant Sphero®GEL contributing to repairing processes at the site of tissue lesion have been experimentally and clinically confirmed. Preclinical and clinical trials were performed by the FGU Scientific Research Institute of Transplantology and Artificial Organs, ZAO NeuroVita Clinic, the Troitsk Hospital of the Russian Academy of Sciences, the Civil Aviation State Clinical Hospital, the S.P. Botkin State Clinical Hospital.

The clinical trials have shown highly efficient functional properties of the Sphero®GEL matrix when applied as:
- a biologically active artificial synovial fluid for therapeutical treatment of knee joints deforming arthroses;
- implants for surgical intervention of peripheral nerves conductance disorder;
- implantable carriers for transplantation and holding stem cells for spinal cord injury treatment.

It was just the Sphero®GEL matrix that, after it had been tested on animal models of spinal cord injury in the ZAO NeuroVita Clinic for three years, provided the basis to the neuroendoprosthetic system used in the proposed method. To establish a cell system with the stimulators of tissue regeneration, further perfusion of specific cell preparation into the Sphero®GEL matrix was proposed in the course of experimental and clinical trial of the matrix. The main challenge of the ACBP NEPS development was to select basic components of the cell preparation and to determine their concentration in 1 ml of the biodegradable Sphern®GRTJ matrix.

Endothelial cells with the CD34+ marker and neural stem cells possess the property of target oriented migration to lesion sites. Transplanted cells form clusters of progenitor cells in the brain/spinal cord tissue. This phenomenon became essential in solving the problem of the regeneration of the injured brain/spinal cord. It was, however, only after long-term animal experiments and 32 surgeries on humans, that the optimal combination of the biopolymer with the cell preparation and the regeneration stimulators has been found, which allowed achieving maximal clinical and neurophysiological effect of surgery in tissue engineering of brain/spinal cord and thus resulted in the creation of the ACBP NEPS.

The ACBP NEPS represents a prepared an artificial, not occurring in nature, analogue of a nervous tissue with its basic cell elements (neurons, neuroglial cells, endotheliocytes, etc.) and a polymer matrix with specified parameters of biodegradation (from 8 to 12 months). The consistency and plasticity of the ACBP NEPS allow for adequate modeling of neuroimplant in damaged anatomical structures of the brain and also provide for local stimulation of regeneration processes in the lesion site. The ACBP NEPS is able to fulfill bridging and nourishing functions to facilitate growth of injured axons through pathologically modified regions of brain/spinal cord tissue.

The amount of cells used in the method is substantially more that nature can supply to a tissue damage area. All the cell components used in the ACBP NEPS result from culturing the cells and obtaining cell lines after several (no less than two) cell passages in the culture during a number of days. After that, they are washed out of the culture medium in a physiological solution (0.9% solution of NaCl) by centrifuging. Additionally, the system can be subjected to electromagnetic radiation at 1-10 GHz before implanting.

NSC contained in the cell preparation of the ACBP NEPS can reconstruct the injured nervous tissue and, first of all, provide for the restoration of the gray matter of the spinal cord, while NGEC can stimulate differentiation of blood precursor cells into astrocytes and oligodendrocytes that can restore the white matter and be a source of the cells capable of remyelinizing damaged axons. Adding hematopoietic stem cells (CD34+CD45−) oriented for endotheliocytic differentiation and, hence, presenting the source of EC, to the cell preparation enhances development of new vessels, leads to the rapid formation of a microcapillary vascular network in the endoprosthesis, improves local blood supply. The use, as a component of the cell preparation, of non-hematopoietic stem cells being in the peripheral blood mononuclear fraction (MN) after stimulation by colony-stimulating factors leads to the production of a large amount of growth factors that significantly contribute to axon regeneration.

The use of various cell preparations in the Sphero®GEL matrix in clinical practice has showed that the best clinical and neurophysiological outcome is achieved from a specific ratio of certain cell preparations in the Sphero®GEL matrix, rather than from isolated application of the matrix and intracerebral or intramedullar administration of these cell cultures. The understanding of helped create the specific artificial microenvironment for the damaged axons, close, by its cell structure, to that in natural tissue of a developing brain/spinal cord.

The production of a suspension of cultured NGEC and NSC follows a conventional procedure. The source of these cells is a fragment of olfactory sheath of the patient's nose, which fragment is isolated in the course of otolaryngologic endoscopic surgical manipulation. Preparations of the hematopoietic stem cells, which are the source of EC, as well as non-hematopoietic stem cells residing in the mononuclear fraction (MN) are produced according to the technique described in the RU patent No. 2283119, incorporated herein by reference, and in the registration certificate No. FC-2006-/151 of Jul. 1, 2006 of the Federal Service on Surveillance in Healthcare and Social Development.

The proposed method of ACBP NEPS production (and the method of neurosurgical operation based thereon) can be implemented only under conditions of neurosurgical operation room of a surgical department and anesthesiology and resuscitation department of a multifield hospital licensed for medical activities involving high technologies in neurology, neurosurgery, hematopoietic stem cells harvest and application of cell technologies by neurosurgeons and anesthesiologist-resuscitators trained for the use of cell technologies. The hospital should be equipped with present-day diagnostic means (MRI, spiral computer tomography, angiographic equipment, cytofluorometer, blood separator) or have agreements with institutions equipped with these means. A laboratory performing certification of autologous hematopoietic stem cells of peripheral blood (AHSCPB), NSC, NGEC and BC must be licensed as a laboratory authorized for cell techniques application, meet the GLP (Good Laboratory Practice) standard and be able to perform complete analysis of a cell preparation in the scope recommended by the European Bone Marrow Transplant Registry. Also, the laboratory must be capable of testing a biopreparation for sterility, toxicity, and of culturing the material, i.e. be equipped with a sterile box with a laminar safety cabinet, $CO_2$ incubator, bifocal microscope and a kit for culturing. The personnel must be additionally trained in transfusiology.

The procedure of use of the ACBP NEPS for the proposed method consists of several consecutive stages:
I—specific examination of a patient;
II—harvest and preparation of the biomaterial (including the proposed method of the ACBP NEPS production), and
III—reconstructive neurosurgical operation on the spinal cord or brain with intraoperative preparation of the ACBP NEPS and its implantation.

Stage I. Specific Examination of a Patient

At this stage, the requisite clinical and paraclinical examination of a patient according to standard protocol is performed. Diagnostic parameters of the site of lesion are analyzed, the strategy of tissue engineering for brain or spinal cord is developed, indications and contraindications for ACBP NEPS implantation are established, as well as the tune schedule for every stage is set adjusted for the results of examination. If necessary, cell transplantation is mathematically simulated, and the volume of the cell preparation to prepare the ACBP NEPS according to MRI data is estimated. This stage should not be formal testing and examination. It is at this very stage where absolute and relative contraindications are determined, as well as medical and social prognosis of the surgery in tissue engineering on the brain and spinal cord for the patient. Inasmuch as the intramedullar and/or intracerebral introduction of NCS and NGEC preparations is planned, main attention should be given to immunochemical characteristic of blood and CSF of the patient. Additional introduction of neurospecific proteins during the transplantation of neurons and neuroglia-containing cells in the course of the surgery, combined with initially high value of neurospecific antigens in the patient's blood and CSF, can further deepen self-destructive process in the CNS. At the same time, introduction of neurospecific proteins during transplantation of neurons and neuroglia-containing cells in the course of the surgery, combined with the initial presence of antibodies to neurospecific antigens in the patient's blood and CSF can trigger or enhance the autoimmune process, and in certain cases contribute to the autoimmune lysis of injured tissue. The patients with antibodies to neurospecific proteins and immunological deficit are not recommended as candidates for such surgeries.

Stage IL Harvest and Preparation of the Biomaterial

II.1. Composition of the Heterogeneous Implantable Gel Spllero®GEL

The Sphero®GEL composition is produced according to the method described in the above-mentioned RU patent No. 2283119 incorporated herein by reference. It comes in the injection formulation in syringes of 1, 2 and 5 ml.

At room temperature, the heterogeneous matrix Sphero®GEL presents an elastic mass which is stable at long storage, not susceptible to syneresis (separating out of liquid). At the temperature of 37° C., viscosity of the biopolymer matrix sharply reduces due to a weakly cross linked liquid component, while the physical condition of a globular (solid) component does not change. Immunogenicity of the obtained matrix is sufficiently low.

Antibiotics, antiseptics, stimulators of regeneration and anticoagulants can be introduced into the matrix immediately before surgical intervention as additional components. The antibiotics can include penicillins (such as benzylpenicillin, cloxacillin, ampicillin), cephalosporins (such as cephaloridin, cefuroxime, cefotetan, ceftazidine), carbapenems (such as meropenem), monobactams (such as aztreonam), aminoglycosides (such as streptomycin, gentamicin, amikacin), tetracyclines (such as tetracycline, minocycline), macrolides (such as erythromycin, azithromycin), lincosamides (such as lincomycin), antibiotics of the peptide group (such as polymyxin B, polymyxin M, ristomycin, bacitracin). Methyluracil, leucogen, adenosine triphosphate acid (ATP), pentoxyl, potassium orotate, inosine, etadenum can, for example, be used as stimulators of cell regeneration.

Antibacterial and antiviral components, as well as anti-aggregational agents can be additionally introduced into the Sphero®GEL composition. The stimulators of cell regeneration are perfused into the Sphero®GEL directly in a surgical room in the volume not exceeding 0.2 µl per 1 ml of the matrix.

The Sphero®GEL matrix introduced directly in the injury site is replaced over time by the original tissue with no scar formation.

Advantages of the Sphero®GEL matrix used for implantation in injured brain and spinal cord are as follows:
   multifunctionality (performs supporting and trophic functions for cell cultures and stimulates axon regeneration and neovascularization);
   high biocompatibility of the final product, as well as of the products of its biodegradation, at the protein and cell levels;
   capability to stimulate proliferation and differentiation of neural cells;
   controllable period of biodegradation varying from several weeks to several months, the final products of the biodegradation being water and carbon dioxide;
   cavitation capacity at the immediate contact with biological media, which provides for neovascularization;
   capability of being sterilized without affecting medical and biological properties.

II.2. Processing and Production of the Cell Preparations

II.2.1. Production of Stem Cells

The procedure can be conditionally subdivided into two stages, namely mobilization of stem cells into peripheral blood and stem cell harvest.

II.2.1.1. Mobilization of Stem Cells into Peripheral Blood

To increase the number of stem cells in peripheral blood, a donor gets 8 subcutaneous injections of granulocyte colony-stimulating factor (G-CSF) every 10 to 12 hours for 4 days. G-CSF is a pharmaceutical obtained by gene engineering and absolute analogue to human factor. The first three days, the dose makes 2.5 µg/kg and the last day, the dose is doubled. The blood is checked daily and ultrasound examination of abdomen is to be done at day 4 to 5.

II.2.1.2 Stem Cells Harvest

On day 5 since the G-CSF stimulation has started, stem cells are harvested in a blood separator of COBE-spectra type using a disposable system for separation and standard solutions. The procedure lasts 3 to 4 hours depending on the speed of the procedure, weight of the patient and blood test results. In the course of the procedure, blood is sampled from a vein, processed inside the separator, the stem cells are sampled, and the rest components of blood are returned to the donor through another vein. Veins are accessed by the puncture of two peripheral veins or by dual-lumen central catheter inserted for the duration of the procedure into the subclavian vein. Average volume of the obtained material varies from 300 to 400 ml. The gathered material is evaluated by two parameters: by the total number of nuclear cells (NC) in the sediment and by the number of CD34+ cells per every kilogram of the patient's weight. NC in the sediment are determined by counting in Gorjaev's chamber before any manipulations. The percentage of the CD34+ in the cell preparation obtained in the course of cytapheresis is determined by a flow cytometry procedure.

II.2.2. Specification of Peripheral Stem Cells

A subpopulation composition of the CD34+ is determined by cytofluorometry with the method of triple-labeling (simultaneous staining of the cells with antibodies, loaded with various dyes, to three different antigens).

II.2.3 Standardization of the Preparation

The number of precursor cells is determined by cytofluorometry a direct immunofluorescence test (DIT).

A method of double labeling is used with staining cell substrate by monoclonal antibodies (MCA) to both—a CD34 antigen, that is the main marker of a hematopoietic stem cells pool, and a CD45 molecule, which is a common leukocyte antigen characteristic for all hematopoietic stem cells. Such method permits direct calculation of the ratio of CD34+ cells and all hematopoietic (CD45+) cells in the product.

To evaluate non-specific binding levels, a part of the cells is stained by isotypic controls such as conventional mouse immunoglobulins IgG1 of isotype (IgG1), labeled with dyes analogous to the label of the monoclonal antibodies (PE, FITC, PerCP) in use.

II.2.4 Preparation of Cell Tests

Before the reaction, the cells of peripheral blood and cytapheretic product are cleared from erythrocytes by a standard lysis procedure and then are washed in buffered saline with bovine serum albumin (BS-BSA) by centrifuging at 1,000 g for 5 minutes. BS-BSA can be replaced with the TC Hanks solution or TC Medium 199.

Method of Lysis of Erythrocytes 1. 2 ml of the lysing solution is added to 0.2 to 0.5 ml of the cell sediment, mixed and incubated till the solution is clear (laked).

2. The cells are washed twice by the 199 medium in the centrifuge (1000 g, 5 to 7 min).

The selected cells are subjected to the DIT in a 96-socket plate, a plate with the following 3 sockets being used to count peripheral HSC in any product:
  unstained cells;
  cells stained by isotypic controls labeled according to the labels of the MCA used;
  cells stained by the MCA both to the antigens CD34 and CD45.

It should be especially noted that MCA to CD34 were preferably phycoerythrin (PE)- or peridinin chlorophyll (PCP)-labeled, since these fluorochrome data have a higher level of specific signal as compared with fluorescein isothiocyanate (FITC).

Optimal to count CD34+ cells are antibodies to CD34 of HPCA-2(8G12) clone, isotype IgG1.

Thus, the reference panel looks as follows:
1. IgG 1 PE control+IgG1 FITC control;
2. IgG 1 PE control+MCA to CD45 FITC;
3. MCA to CD 34 PE (HPCA-2)+MCA to CD45 FITC.

II.2.5 DIT Testing

1. No less than 500,000 cells per a socket are inserted into the sockets.

2. Further, a cocktail of antibodies according to the reference panel is introduced into each socket and carefully resuspended by a pipette. 10 µl of each MCA per a socket is taken, the total volume of MCA in the socket being 20 µl.

3. The cells are incubated with antibodies for 30 minutes at 4° C. (a bottom shelf of a conventional refrigerator).

4. The incubation over, the cells are twice washed from unconjugated antibodies by the 1,000 g centrifugation for 5 to 7 minutes.

5. The cells are put into special plastic tubes to count on a flow cytometer.

6. The volume of cell suspension in every tube is brought to 200 to 5000 by adding PBS-BSA.

The count should be done immediately after the testing.

II.2.6 Count and Record on Flow Cytofluorometer

Reaction is assessed on a flow 5-parameters cytometer. The scheme is applicable for a flow cytofluorometer of any configuration.

The CD34+ cells in peripheral blood represent a minor cell population. Even under the condition of preliminary hematopoietic stimulation, the maximal percentage of these cells is 1.0 to 3.0%. Therefore, to count these cells, no less than 20,000 cell events have to be accumulated in each analyzed sample.

Cell collection and analysis is performed in the gate of CD45+ cells, which includes all hematopoietic cells, the gate herein being understood as the event accumulation region restricted by certain parameters. In this case, by SSC/FL-1(CD4SFITC). That is, the abscissa axis of a dot cytogram will show all CD45+ events. On the ordinate axis (SSC parameter—side light scattering), the cell events will be located according to their granularity (a cytometric term, rather than a morphologic one), The count of the absolute number of CD34+ in 1 µl of blood and of cytoconcentrate was fulfilled based on the number of leukocytes in a hemogram on the day of testing.

II.2.7. Principle of Detecting CD34+ Cells in Hematopoietic Tissue. Recording Samples 1. Region of analysis/gate selection. Menu of cell samples registration Acquisition is open on the appliance. At the first stage in a setup mode (a mode of cell sample review without recording), samples No. 1 (IgG1PE+IgG1 FITC) and No. 2 (IgG1 PE+CD45 FITC) are viewed and CD45+ events are detected. These events are located to the right from $10^1$ values (an average threshold value of specific signal level for the FITC fluorescein) on the x-axis—FL-1 (CD45+ cells) and are clearly visualized in comparison with the control sample No. 1.

According to sample No. 1, the entire region located to the right from major cell density is confined, that is the gate that includes only CD45+ events in sample No. 2 and contains a minimum of cell events in sample No. 1.

2. The appliance is switched to the recording samples mode (Normal), and sample No. 1 is collected and recorded per 20,000 cell events without a gate (the whole cell population). Recording of the sample in the gate is impractical as MCA to CD45 antigen are absent in it. As shown above, the sample is required for the correct selection of the gate containing only CD45+ events.

3. Samples Nos. 2 and 3 are collected and registered in gate CD45+. The gate is identical for both sample No. 2 and sample No. 3, i.e. gate parameters are not changed during sampling. The minimum of cell events equals 20,000 for each sample.

II.2.8 Recorded Samples Analysis

1. The appliance is switched to the menu of recorded samples analysis (Analysis). Then, sample No. 2 cytogram (dot-plot) is opened in SSC/FL-2 parameters, in gate R1-CD45+ (the gate was chosen previously when recording collection and was automatically transferred to the analysis mode). Thus, the y-axis will display the SSC parameter, i.e. granularity of events in the analyzed gate, and the x-axis will display FL-2 that is the detector reflecting levels of nonspecific binding for the phycoerythrin stain, which levels are detected by antibodies to mouse immunoglobulin IgG1PE.

2. The control marker is set on the received cytogram, so that almost no cell events appear in the right low quadrant. In average, the values for the vertical bar of the marker will make about 130 (to the right from $10^2$), and for the horizontal marker bar, the average values will be 60 that corresponds to SSC-low, i.e. the cells with minimum cell inclusions. Therefore, the levels of nonspecific binding will be equal or close to zero.

3. Automatically switch to sample No. 3. All indications of the appliance for sample No. 2 are saved, i.e. cytogram is open in SSC/FL-2 parameters, the gate chosen earlier during the collection on the CD45+ cell events is saved, and the meanings of the control marker set on sample No. 2 are saved too. However, on this cytogram, the x-axis displays specific CD45+ events rather than the levels of non-specific binding as in the second sample. CD45+ percentage is displayed by the appliance automatically.

II.2.9 AHSCPB Cryopreservation

II.2.9.1. AHSCPB Fraction Isolation

Separated cells are concentrated by centrifuging at 2,000 r/m for 10 minutes at +18° C. Plasma is maximally removed from the container by a manual plasma extractor, the remaining cell volume being of 40 to 60 ml.

II.2.9.2. Adding Cryoprotector

Purified dimethyl sulphoxide (DMSO) is used as a cryoprotector of hematopoietic cells. Equal volume of polyglucin with DMSO is added to the obtained cells at continuous stirring. DMSO reacts with polyglucin exothermally with moderate heat liberation. DMSO concentration in polyglucin is 10 to 12%. Thus, its final concentration in the material being frozen will make 5 to 6%.

Application of polyglucin permits to use half as much of the DMSO amount, икштлштп ще to 5 to 6% in the final concentration because polyglucin can disaggregate cells thus improving penetration of cryophylactic into the cells. Beside that, polyglucin (6% dextran) is a cryophylactic per se.

II.2.9.3. Cell Count

The next stage necessarily involves counting of nuclear cells, as well as CD34+ cells to be frozen.

II.2.9.4. Choice of the Optimal Volume of Frozen Material

To provide the best conditions for cryopreservation, a correlation of the plastic container volume and the volume of the material to be frozen therein, as well as the concentration of frozen cells are important. It has been determined that the optimal concentration of the frozen cells is from $40 \cdot 10^6$ to $100 \cdot 10^6$ cells per 1 ml.

II.2.9.5. Stem Cell Freezing

Depending on the final volume of material to be frozen, a proper number of polymer tubes (15 to 20) for deep freezing should be chosen. Then, the cell suspension is placed into a container for cryopreservation.

To freeze the tubes with cell suspension, they are put into a programmed freezer or a laminated plywood container (10 mm of total thickness) with a tight lid and of the size consistent with the size of the tubes. Then, the container with the material to be frozen is put into liquid nitrogen vapor at minus 165-170° C.

The speed of cooling of the material at the temperature from 0° C. to minus 40° C. is 1.1 degree per minute. This cryopreservation method levels crystallization plateau, that usually is clearly seen at program freezing in an electronic device, and the composition of the frozen material remains unchanged when stored.

In one or two hours after the beginning of freezing, the container can be transported to a warehouse where it will be stored in liquid nitrogen or its vapor till transplantation.

II.2.10. Preparing AHSCPB to Administration. Defrosting Hemopoietic Stem Cells The product is defrosted immediately before transplantation at 37 to 40° C. in a water bath till the moment of transition of the frozen product into a liquid state. Then, the mobilized hemopoietic stem cells are deposited by centrifugation at 1,500 r/m to the bottom of a centrifugal plug, the supernatant is drained, and 1 ml of 0.9% NaCl physiological solution is added. The procedure is repeated twice. The product of the defrosted autologous stem cells can be administered within 6 hours after its preparation. If the product was not used during this time, it must be recycled.

II.2.11 Taking NSC and NGEC

Nasal mucosa has to be endoscopically taken with informed consent of a patient. Nasal cavity was subjected to vasoconstriction by 0.1% solution of Xylometazoline. Under contact anesthesia with 10% solution of Lidocaine and local anesthesia with 1% solution of Procaine, a 3×4 mm size fragment of an upper portion of nasal septum mucosa is exsected. Bleeding is suppressed by cotton plugs with solution of Xylometazoline and hydrogen dioxide. The plug is removed 24 hours after the surgery in the absence of any nosebleed. In case of even slight bleeding, the nasal passages are repeatedly plugged for 24 hours.

II.2.12 Method of Obtaining and Culturing NGEC Olfactory Epithelium (Ensheathing Cells)

Olfactory epithelial tissue was sampled from the upper third of superior nasal meatus of adult patients. The obtained tissue was washed in the Hanks solution that contains antibiotics (Streptomycin, Penicillin) and antimycotic (Amphotericin). The tissue sample was minced and incubated in a Trypsin (0.05%) and EDTA (0.02%) solution (40 min, 36.5° C.). The tissue was dissociated by multiple pipetting, centrifuged, and sedimented cells were washed with the Hanks solution with 5% serum. The total number of cells in the suspension and percentage of viable cells were determined in a Gorjaev's count chamber by trypan blue staining. The cells (whose final concentration was 100,000 cells per ml) were cultured in 12-well trays on a polylysine/laminin substratum for 10 to 15 days (5% $CO_2$, 36.5° C.) in the following medium: DMEM/F12 (Gibco), fetal calf serum 10% (Gibco), glutamine 2 mM (Gibco), glucose 0.8%, a mixture of insulin, transferrin and sodium selenite (Gibco, 1:100), the HEPES buffer (10 mM), human neuregulin-1 β-1/heregulin 1-β-1 EGF domain 2 ng/ml (R&D systems). The medium was replaced every 3 to 4 days. The dense monolayer having being developed, the cells were removed for subsequent passages from substratum by the trypsin/EDTA solution, washed with the Hanks solution, and reseeded into flasks with polylysine/laminin substratum (25 $cm^2$, 10,000 to 12,000 cells per $cm^2$). After 3 to 4 passages, the cells were removed from substratum by the trypsin/EDTA solution, washed with the Hanks solution, and the obtained suspension was either used for transplantation or frozen with cryoprotector (10% serum, 90% EDTA) and stored in liquid nitrogen at minus 70° C. For transplantation, the cryopreserved cells were defrosted; their viability was detected by trypan blue staining. Control tests showed that no less than 90% of cells retained viability after storage.

For cytochemical identification of olfactory epithelial glial cells, a part of suspension was cultured after every passage on a cover slip (22×22 mm) in Petri dishes for a week. Primary antibodies to glial fibrillary acidic protein (GFAP, 1:6; monoclonal antibodies obtained in the Immunochemical Laboratory of the Serbsky State Research Centre of Social and Forensic Psychiatry), to nestin (Chemicon International, CA, 10 µg/ml) and to low affinity nerve growth factor receptors (p75, Chemicon International, Inc., 10 µg/ml) were used for immunocytochemical analysis. The obtained preparations were analyzed and photographed by fluorescent microscope Leica DLMB.

II.2.13 Method of Isolation Ami Culturing of NSC of Olfactory Sheath of Patient's Nose The tissue of the olfactory sheath including olfactory epithelium and a layer of a connective tissue (lamina propria) is isolated from patients with a spinal cord injury and processed according to a standard culture protocol.

10 by 5 mm size fragments of mucosa dissected under local anesthesia from the upper part of superior nasal meatus were accepted for the research. The sampled tissue was delivered to a laboratory in the cool Hanks solution without $Ca^{2+}$ and $Mg^{2+}$ (HBSS) containing antibiotic and antimycotic agents (1:100; Gibco). Delivery time does not exceed 2 hours. After repeated wash in the same solution, blood vessels were removed from mucosa, then the tissue was minced and incubated for 40 minutes at 36.5° C. in the 0.25% trypsin/EDTA solution prepared on the 0.01 M phosphate buffer (PBS, pH 7.4). The activity of ferments being blocked by the DMEM medium (Gibco) that contained 3% of serum, the tissue was washed in three changes of the Hanks balanced salt solution (HBSS; Sigma) and dissociated by repeated pipetting in a nutritive medium. Medium composition: 90% of minimum Eagle medium (MEM, Sigma), fetal bovine serum (FBS, Gibco, Invitrogen), 0.8% of glucose, 2 mM glutamine (Gibco), B27 supplement (Sigma), HEPES 20 mM, growth factors (only for primary cultures) namely fibroblast growth factor (FGF2, 1 ng/ml, Sigma), neural growth factor (NGF 2 ng/ml, Sigma).

The obtained cell suspension is centrifuged (3 minutes at 1200 r/m), the sediment is resuspended in a nutritive medium of the same composition.

The number and viability of the dissociated cells are checked in the Gorjaev's chamber after 0.1% trypan blue staining. Cell suspensions with 85 to 95% of viable cells are only used for further culturing.

The dissociated cells ($5 \cdot 10^5$ cell/ml) are cultured in 12-well trays on polyllysine/laminin substratum for 14 days (365° C., 5% $CO_2$). One third of the nutritive medium is replaced two times a week. Primary culture, after a confluent cell monolayer is formed, is removed by the trypsin/EDTA solution. The cells are resuspensed in the nutritive medium after washing in HBSS and centrifuging. The cell suspension (10,000 to 12,000 cell/cm²) is placed into 12-well trays or dishes with square of 25 cm². In this way, the cultures are passed four times until the confluent monolayer has been formed. Free floating and attached to substratum neurospheres formed in the cell monolayer are selected by Pasteur pipettes and dissociated by the ferment processing method described above. The selection of the neurospheres permits to separate them from accessory glial cells, fibroblasts and stromal (foot) cells attached to the substratum. The cell suspension of the neurospheres, after washing and centrifuging, is resuspended in the nutritive medium and cultured in 12-well trays (10,000-12,000 cell/cm²) and on cover slides (18×18 mm) in Petri dishes until the confluent monolayer has been formed. The obtained cultures are used for cytological and immunocytochemical tests. A part of the cells of last passages is frozen in cryopreservation medium (90% serum, 10% dimethyl sulfoxide) and stored in liquid nitrogen.

II.2.14 Immunocytochemical Tests

The cell monolayer is fixated in a 4% solution of paraformaldehyde prepared on 0.01 M phosphate buffer (pH 7.4) for 30 minutes. After PBS washing (3×10 min), the cells are incubated for 24 hours at 4° C. with primary antibodies to β-tubulin (1:300; Chemicon), nestin (1:100, Chemicon) and neuronal specific enolase (1:100, the antibodies are obtained in the applicants' laboratory). After PBS washing, the cells are successively processed by biotinylated antibodies with avidin-biotin complex (ABC, Vector Laboratories, Inc), and the diaminobenzidine solution prepared on phosphate buffer (DBA 0.5 mg/ml, hydrogen dioxide 0.03%). The preparations are dehydrated and placed into synthetic resin under cover slides (Entellan, Merck).

II.2.15 Method of Isolation of CD 34+ Endothelial Cells from the Preparation of Mobilized Stem Cells To obtain a cell preparation of endothelial cells (EC), a standard procedure of separation of stem hematopoietic cells CD34+ CD133+ from leukoconcentrate of mobilized peripheral blood and a magnetic beads separation (CD34+) followed by a short-term standard cell culturing was applied. The culture medium consists of Iscove's modified Dulbecco's medium with added 0.5 g/l of serum albumin, 0.39 µg/ml of human insulin and 60 µg/ml of transferrin. 100 ng/ml of stem cell factor (SCF), 20 ng/ml of Flt3(Flt3L) and 20 ng/ml of thrombopoietin (TPO) are added to the culture medium. The culturing regimen is the following: the cells are cultured at 37° C. in the atmosphere of 5% $CO_2$, and fresh medium and cytokines are added every three days, the period of culturing making 5 to 7 days.

To avoid contamination of the cell preparation by autologous mononuclears, erythrocytes, thrombocytes and other hemocytes, the leukoconcentrate is purified therefrom. The preparation of purified mononuclears is prepared from the cryopreserved and unfrozen cell preparation of mobilized autologous stem cells (MASC) by outwashing 10% DMSO solution therefrom by means of triple centrifuging at 2,000 r/m with physiological solution of 0.9% NaCl.

Stage III. Reconstructive Neurosurgical Operation on the Spinal Cord or Brain, Intraoperative Preparation of ACBP NEPS, Implantation of ACBP NEPS

III.1. Intraoperative Preparation of ACBP NEPS

The cell preparation is prepared in sterile conditions either directly in a surgical room (ex tempore) or in advance in a culture laboratory (to be implanted within 6 hours). The amount of the ACBP NEPS is defined depending on the volume, type and location of the injury. A provisional calculation of the required amount of the ACBP NEPS is performed according to MRI or CT imaging results of the brain or spinal cord (BSC). The ACBP NEPS is prepared as follows. The cell preparations in the above-mentioned proportions are mixed in a sterile tube in required volumes and allowed to stir by means of 2 to 3 syringe intakes from, and discharges back into, the tube. The Sphero® GEL preparation is taken out of a refrigerator and warmed up to 37.5 to 38° C. A disposable syringe of the volume corresponding to the required calculated volume of the ACBP NEPS is used. The plunger is removed from the syringe and the needle cannula is closed with a rubber or plastic plug (the syringe is used as a tube). 1 ml of the Sphero®GEL is placed on the bottom of the syringe tube and up to 1 ml of the cell preparation is added. The tube is centrifuged for 2 minutes in a minicentrifuge at 2,000 r/m. The liquid component of the cell preparation is perfused into the Sphero® GEL during centrifuging. If a larger volume of the ACBP NEPS is to be prepared, the above mentioned procedure is performed in layers in the syringe tube by placing the Sphero®GEL and the cell preparation alternately in layers as in a sandwich and then centrifuged for 2 to 3 minutes. The plunger is returned into the syringe and the air is removed therefrom. A plastic sterile venous catheter is put on the syringe cannula, which catheter will be used for implantation. After the preparation of the ACBP NEPS, it is left for 30 to 40 minutes in the syringe under sterile conditions at room temperature (20 to 22° C.) to cool down and to acquire toothpaste consistence. Then, the ACBP NEPS can be implanted.

III.2 Reconstructive Surgery on the Brain or Spinal Cord and ACBP NEPS Implantation The plasty of SC defects is performed with the use of the ACBP NEPS in a standard neurosurgical operation of decompressive laminectomy at the level of injury by opening dura mater (DM) and performing radiculomyelolysis of the site of injury. The ACBP NEPS is placed on the surface of spinal cord defect and modeled along the injury. In case of intramedullar or intracerebral implantation, the ACBP NEPS is isolated from direct impact action of CSF. Hence, an intramedullar cyst (cysts) of the SC is opened, drained and the ACBP NEPS is implanted inside the SC cyst. Microsurgically modeled in the gap area of the SC in case of neurotmesis of the SC is a conduit, that is a tube-like conductor (TLC), the walls of which are formed either from the inner leaf of the DM of the patient or a hip muscle fascia of the patient or artificial arterial (aortal) graft attached to the DM of the patient. The ACBP NEPS is implanted inside the TLC. Proximal and distal ends of the injured spinal cord are attached (tunneled and sutured to the DM) to the formed conduit.

The SC plasty being completed, the DM is closed and sutured with the inner leaf of the autologous DM or an artificial DM, then the site of the DM plasty is covered with a standard biopolymer glue (like Tissucol®). The implantation of the ACBP NEPS into brain defects should be done after evacuation of the content (CSP, detritus, etc) out of cystic cavities of the brain during either open neurosurgical operations or in the course of functional neurosurgical interventions (stereotaxis, endoscopic manipulations, etc.) or during the implantation of the ACBP NEPS in vegetative ganglia. It was shown that the ACBP NEPS degrades within 12 to 24 months, and the site of the prosthesis is transubstantiated, partially or completely, by fibers of autologous nervous tissue. Subsequent post-interventional neurovisualization of the BSC plasty area with the use of MRI imaging 8 to 12 months after the intervention allows for verification and evaluation of the morphology of the structure of the reconstructed BSC tissue.

After the ACBP NEPS implantation, the patient is under observation for 10 days 24 hours a day. An intensivist together with an attending doctor should control the condition of the patient to assess complication risks. Besides, regular observation by a neurosurgeon and a neurologist is recommended, who should work in close cooperation with hematologists, transplantologists, immunologists and laboratory specialists.

The main efficacy criteria of this intervention are improvement of neurological symptoms (motor, sensation and bowel and bladder functions). The period of first manifestation of expected results is highly individual and depends on the scope of the BSC injury, the length of the post-injury period, level of compensation of injured functions. Therapeutical efficiency varies from 7 days to 48 months after tissue engineering surgery and is evaluated by the indexes of ASIA (American Spinal Injury Association), FIM (Functional Independence Measurement) and neurophysiological methods of testing (cerebral EEG mapping, transcranial magnetic stimulation, somatosensory evoked potentials, electroneuromyography and complex urodynamic testing).

INDUSTRIAL APPLICABILITY

Efficiency of the present invention was evaluated in the patients with consequences of brain and spinal cord injuries in comparison with conventional surgical treatment. To objectify received clinical results, specific ASIA and FIM indexes were involved, as well as data received by MRI, electroneuromyography, cerebral EEG mapping, complex urodynamic testing, immunochemical tests of blood and CSF. The trial was done in 50 patients. Surgeries in tissue engineering with the ACBP NEPS implantation were given to 30 patients with severe traumatic disease of the spinal cord. All the patients enrolled into the trial were subdivided into two groups. The $1^{st}$ group (main, 30 patients) consisted of the patients who had been operated with the ACBP NEPS implantation, whereas the $2^{nd}$ group (control, 20 patients) included patients that received conventional surgical treatment (decompressive laminectomy, microsurgical radiculomyelolysis, drainage of intramedullar cysts, DM plasty). Distribution of the patients by age and gender is shown in Table 1.

TABLE 1

Distribution of patients by age and gender

| | $1^{st}$ group | | | | $2^{nd}$ group | | | |
| --- | --- | --- | --- | --- | --- | --- | --- | --- |
| | M | | F | | M | | F | |
| Age (years) | Number | % | Number | % | Number | % | Number | % |
| 14-19 | 2 | 9 | 1 | 12.5 | 3 | 20 | — | — |
| 20-30 | 11 | 50 | 2 | 25 | 5 | 33.3 | 5 | 100 |
| 31-40 | 7 | 31.8 | 4 | 50 | 6 | 40 | — | — |
| 41-50 | 1 | 4.4 | 1 | 12.5 | 1 | 6.7 | — | — |
| 51-60 | 1 | 4.5 | — | — | — | — | — | — |
| Total | 22 | 100 | 8 | 100 | 15 | 100 | 5 | 100 |

Comparison of efficiency of SC tissue engineering by the ACBP NEPS implantation for traumatic disease of SC and brain with conventional surgical therapies is demonstrated in FIG. 1. The 1st group shown here presents the patients that received surgical treatment with the ACBP NEPS implantation according to the present invention; the 2nd group is the patients of the control group that received conventional surgical interventions. The efficiency of SC tissue engineering with the ACBP NEPS implantation for the SC injury (SCI) was statistically significant ($p<0.05$) as compared to the control group. The significance ($p<0.05$) was calculated by $\chi^2$ method.

Figure 2:
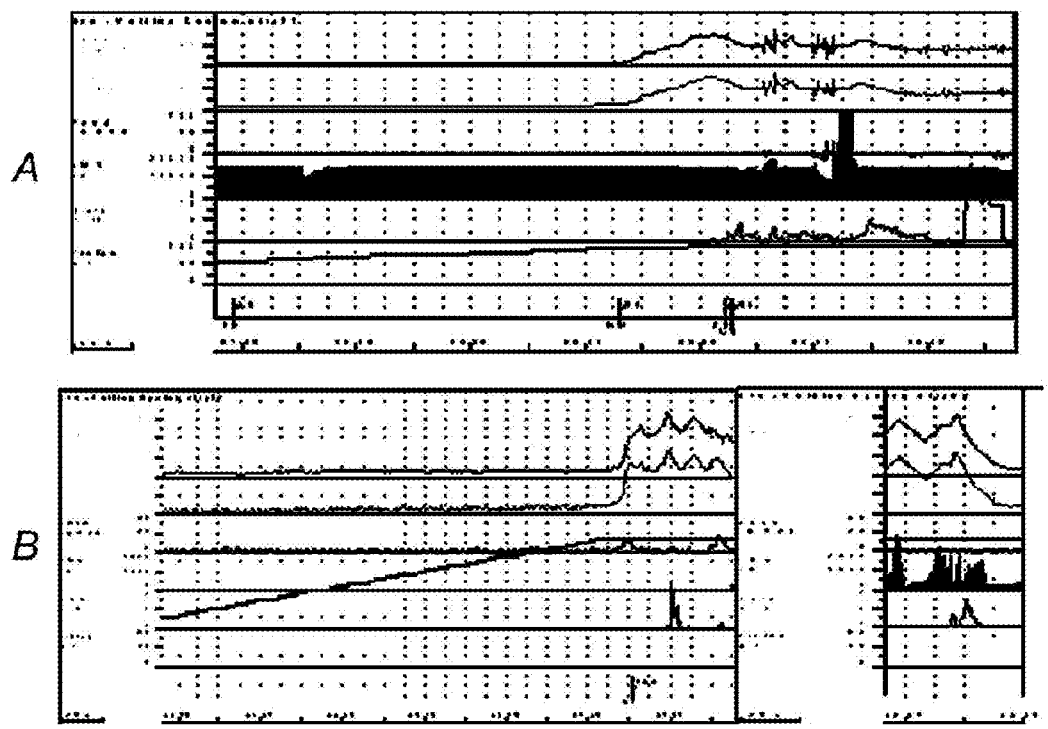
FIG. 2 showing urograms of a patient before (A) and after (B) implantation of the ACBP NEPS according to the present invention.

FIG. 2 shows changes of urodynamic values in patient V. before and after the ACBP NEPS implantation according to the present invention (A-urogram before the treatment, B-urogram after the ACBP NEPS implantation).

The received data are also shown in Tables 2 and 3 and accompanied by clinical Examples 1 and 2.

TABLE 2

Result of treatment of SCI patients after tissue engineering surgeries with ACBP NEPS implantation

| No. | Patient | Injury level | Time after injury, years | ASIA, FIM indexes before treatment | | ACBP NEPS components* | ASIA, FIM indexes after treatment | | Time after treatment (months) | Sensation | Motor restoration | Bowel and bladder control |
|---|---|---|---|---|---|---|---|---|---|---|---|---|
| 1 | B-ev N. V. | C5 | 4 | A | 46 | No. 2 | B | 48 | 11 | T1 | Complete | Partial |
| 2 | P-us M. | T7 | 2 | A | 46 | No. 4 | B | 46 | 10 | T10 | Partial | Partial |
| 3 | Sch-ba F. | C7 | 8 | A | 37 | No. 3 | A | 37 | 11 | T3 | Partial | Partial |
| 4 | T-syan A. | T1 | 2 | A | 24 | No. 3 | A | 24 | 11 | T5 | Partial | Partial |
| 5 | R-ska D. | T11 | 2 | A | 31 | No. 4 | C | 37 | 10 | Complete | Partial | Complete |
| 6 | K-kin A. V. | T10 | 3 | A | 46 | No. 2 | B | 46 | 10 | L2 | Partial | Complete |
| 7 | Al Azzi D-ll | C5 | 3 | A | 57 | No. 4 | A | 57 | 8 | C7 | Partial | Complete |
| 8 | N-shin A. A. | C3 | 7 | A | 30 | No. 2 | A | 32 | 8 | C7 | Partial | Complete |
| 9 | M-t A. | T10 | 2 | A | 18 | No. 4 | A | 18 | 6 | T12 | No | No |
| 10 | D-es P. | C5 | 3 | A | 49 | No. 4 | A | 49 | 1 | T6 | Partial | No |
| 11 | A-yan E. | T5 | 5 | A | 24 | No. 4 | A | 16 | 17 | T6 | Partial | Complete |
| 12 | B-chuk N. N. | T12 | 6 | A | 25 | No. 4 | A | 21 | 14 | Complete | Partial | Partial |
| 13 | Sh-lekh N. | T7 | 5 | A | 35 | No. 4 | B | 27 | 30 | T10 | Partial | Partial |
| 14 | H-m N. | T5 | 2 | A | 24 | No. 4 | A | 18 | 12 | T12 | Partial | Complete |
| 15 | D-ov T. | T4 | 5 | A | 22 | No. 3 | B | 17 | 31 | T7 | No | Complete |
| 16 | Ya-in S. A. | C7 | 4 | A | 53 | No. 3 | A | 50 | 30 | T3 | No | Complete |
| 17 | Sh-ga Ya. | T4 | 16 | A | 36 | No. 4 | C | 24 | 27 | Complete | Partial | Complete |
| 18 | Kh-osh P. M. | T5 | 4 | A | 44 | No. 3 | A | 38 | 24 | T7 | Partial | Partial |
| 19 | L-kov A. S. | T5 | 6 | A | 43 | No. 3 | A | 39 | 26 | T8 | Partial | Partial |
| 20 | A-ev Ye. L. | T6 | 2 | A | 31 | No. 3 | A | 27 | 26 | T10 | Partial | Complete |
| 21 | S-ds E. | C7 | 5 | A | 46 | No. 2 | B | 44 | 15 | C7 | No | Partial |
| 22 | V-ev A. V. | T2 | 2 | A | 44 | No. 2 | B | 37 | 25 | T2 | Partial | Partial |
| 23 | V-der L. | C5 | 2 | A | 66 | No. 3 | A | 66 | 25 | C7 | Partial | Partial |
| 24 | I-va O. A. | T3 | 5 | B | 54 | No. 4 | C | 39 | 25 | T6 | Complete | Complete |
| 25 | Sch-kov S. G. | T8 | 11 | B | 35 | No. 1 | C | 34 | 45 | T9 | Partial | Partial |
| 26 | O-kov A. N. | T7 | 10 | A | 28 | No. 3 | B | 27 | 44 | T12 | Partial | Complete |
| 27 | L-shin P. A. | C6 | 1 | A | 62 | No. 3 | C | 52 | 42 | T4 | Partial | Partial |
| 28 | L-va O. D. | T8 | 6 | A | 27 | No. 3 | B | 15 | 42 | T10 | Partial | Complete |
| 29 | Yu-va O. V. | T12 | 1 | A | 24 | No. 2 | B | 14 | 41 | L2 | Partial | Complete |
| 30 | V-na N. C. | L2 | 4 | A | 19 | No. 1 | A | 19 | 41 | L2 | No | No |

*ACBP NEPS composition:
No. 1: Sphero ®GEL:
No. 2: Sphero ®GEL, MN, EC;
No. 3: Sphero ®GEL, NGEC, NSC;
No. 4: Sphero ®GEL, MN, EC, NGEC, NSC

TABLE 3

Changes in nenrological symptoms in some SCI patients after tissue engineering with ACBP NEPS implantation.

| Patient | Time after surgery (months) | Neurological progress |
|---|---|---|
| V-na | 36 | No neurological progress. After removal of metal construction, the spine became unstable. |
| O-kov | 24 | Deep and touch sensation improved. Movement appeared in left toes. Full control of bladder and bowel, and sexual function restored. |
| Sch-kov | 32 | No significant clinical effect was observed. |
| Yu-va | 19 | Able to stand, to "fix" knees, to walk 12 steps. Bowel and bladder control restored, deep and touch sensation improved. |
| L-va | 15 | Level of sensation moved 25 cm down. Able to move legs when asked, control bladder and bowel. Able to make 15 backwards and 2 to 3 steps forward. |
| D-ov | 6 | Deep sensation restored, as well as function of bowel and bladder. Able to cycle on a stationary bike without assistance. |
| Ya-kin | 5 | Weakness in right arm increased, then restored in 7 months, mosaic improvement of sensation |

TABLE 3-continued

Changes in neurological symptoms in some SCI patients after tissue engineering with ACBP NEPS implantation.

| Patient | Time after surgery (months) | Neurological progress |
|---|---|---|
| V-ev | 4 | Right arm movement improved, sensation in back and buttocks area restored, as well as sexual function. |
| L-kov | 5 | Controls bowels and anus, restored thermal regulation and sweating in lower extremities. Restored movement in toes. |
| A-ev | 7 | Controls movement of both legs, the elements of deep sensation appeared. |
| Sh-ga | 8 | Controlled movement in right leg appeared, no pains in the site of injury. Thermal regulation and sweating fully restored, as well as bowel and bladder function. Able to cycle on a stationary bike without assistance. |
| I-va | 6 | Knee (S < D) and Achilles (S < D) reflexes developed, leg spasticity increased, bowel and bladder functions fully restored. |
| L-shin | 20 | Able to turn in his bed without assistance, to sit. Epicystostoma is removed. Arm movement has improved by 50%, bowel and bladder functions restored. Able to eat, drink, brush teeth, and serve himself without assistance. |

Hence, methods of tissue engineering with the ACBP NEPS implantation according to present invention for severe traumatic injuries of brain and spinal cord (including completely severed spinal cord) can be considered as the method of choice, the efficiency of which reaches 45% in the cases when all traditional methods and treatment approaches are practically inefficient. Conventional surgical approach to the treatment of severe repercussions of BSC traumatic injuries does not result in significant improvement of neurological symptoms, while application of the proposed medical technique considerably ameliorates life quality of the patients with severe SCI and brain injury and significantly add to functional and social independence of the patients (see Tables 2, 3).

To date, the proposed method, along with the above-described method of neurosurgical operation, is the only efficient treatment of patients with repercussions of severe BSC traumatic injuries, including complete anatomical neurotmesis of the spinal cord (with the gap up to 5 cm) and can result in significant improvement of their condition, life quality as well as better social adaptation. Possible return of the patients after brain and/or spinal cord injury to normal social activity brings in higher economic efficiency, considering both return to work activity and reduction of expenses for long-term and inefficient treatment.

Clinical Example No. 1

Patient Sch-ga, Ya., 50. Complaints: steady agonizing girdle pains on the level of left costal arch, absence of voluntary movements in the legs, absence of all types of sensation from the level of inguinal fold, constipation and no controlled urination (catheterizes herself for 14 years).

The patient received the injury on thoracic level of the spinal cord in a road accident in 1991: complicated compression fracture of ThIII and ThIV vertebrae. In early period, lower paraplegia was observed, lower paraanesthesia from the level of the Th15 segment. No surgery was given to thoracic level of spine. The patient has repeatedly received specialized training in rehabilitation centers with no notable effect.

The patient was admitted to Neurovita Clinic on Oct. 2, 2006 to be enrolled into the research program "New Cell Technologies—to the Medicine". At the time of admission, the condition of the patient was compensated. Skin and visible mucosa were clean, of normal color, wet. Regional lymph nodes were not palpable. Chest was of regular shape. Breathing was independent, adequate, and free. Respiratory rate was 16 per minute. Pulse was rhythmical, of a satisfactory quality, 88 per minute. Blood pressure was 120/60. Heart tones were clear, rhythmical. The tongue was pink, wet. Abdomen was soft, painless. The liver was not enlarged, spleen was not palpable. The kidneys were not palpable in the seated position. Sense organs and endocrine glands demonstrated no rough defects. Urination was performed with the help of Foley catheter. Defecation was regular every other day with laxative suppositories. The consciousness was clear. The patient was time, space and personality oriented. Pupils were round, D=S, photoreaction was intact, symmetric. Ocular motility was normal, no nystagmus. No face sensation disorders. The face was symmetric; soft palate was symmetric, moving. Swallowing and phonation were intact. No atrophies, pareses, myofacsiculations of trapezius and nodding muscles were observed. The tongue was on the median line, no atrophies, no fasciculation. Coordination tests were performed satisfactorily. Muscle tone in proximal and distal muscle groups was not changed. No hand muscle hypotrophy. Tendon and periosteal reflexes were moderate, no significant difference between the sides. Arm muscle force scored 5. Abdominal reflexes are not evoked. Muscle tone of leg proximal and distal muscle groups was elevated according to spastic type, 3 points by Ashworth index. Notable hypotrophy of calf muscle was observed. Tendon and periosteal reflexes were brisk, D=S. Pathological reflexes of feet, feet and kneecap clonuses were uncovered. Movements of hip flexor muscles were intact (1 point), as well as of knee extensor muscle (2 points). Pain and temperature para-anesthesia from the level of ThXII, tactile para-anesthesia from the Th4 level. Bowel and bladder dysfunction manifested in constipations and urine incontinence. No meningeal syndrome. Functional evaluation by ASIA index: 56*42*46, level of spinal cord injury-A (complete). Functional evaluation by FIM index was 36%.

The results of complex examination of the patient permitted her inclusion into the research program "New Cell Technologies—to Medicine". The patient received the course of MASC transfusions into subarachnoid space according to the program. The received therapy led to the positive effect manifested in the sensation of bladder filling.

The patient underwent surgical intervention on Sep. 26, 2005 in the NeuroVita Clinic: ThII-ThIII-ThIV laminectomy, meningoradiculomyelolysis, tissue engineering of spinal cord using the collagen containing heterogeneous matrix Sphero®GEL with implanted autologous ensheathing glia-olfactory cells ($2.8 \cdot 10^6$), bypassing the spinal canal with the frame-mounted vascular prosthesis <<Gore Tex>>. Postsurgical period was normal, the wound healed with primary adhesion.

Control examination in two years after the surgery demonstrated compensated condition of the patient. Skin and visible mucosa were clean, of normal color, wet. Regional lymph nodes were not palpable. Chest was of regular shape. Breathing was independent, adequate, and free. Respiratory rate was 14 per minute. Pulse was rhythmical, of a satisfactory quality, 86 per minute. Blood pressure was 110/70. Heart tones were clear, rhythmical. The tongue was pink, wet. Abdomen was soft, painless. The liver was not enlarged, spleen was not palpable. The kidneys were not palpable in the seated position. Sense organs and endocrine glands demonstrate no rough defects. Urination was performed with intermittent catheterization. Defecation was regular every other day with laxative suppositories. The consciousness was clear, time, space and personality oriented. Pupils were round, D=S, photoreaction was intact, symmetric. Ocular motility was normal, no nystagmus. No face sensation disorders observed. The face was symmetric; soft palate was symmetric, moving. Swallowing and phonation were intact. No atrophies, pareses, myofacsiculations of trapezius and nodding muscles observed. The tongue was on the median line, no atrophies, no fasciculation. Coordination tests were performed satisfactorily. Muscle tone in proximal and distal muscle groups was not changed. No hand muscle hypotrophy. Tendon and periosteal reflexes were moderate, no significant difference between the sides. Arm muscle force scores 5. Abdominal reflexes were low, D=S. Muscle tone of leg proximal and distal muscle groups was elevated according to spastic type, 2 points by Ashworth index. Moderate hypotrophy of calf muscles was observed. Tendon and periosteal reflexes were moderate, D=S. No pathological reflexes no clonuses were observed. Hip flexor muscles scored 3 points, knee extensors-2 points, dorsal feet flexors score 2 points, extensors of the $1^{st}$ toe-2, toe flexors-2 points. The patient can "fix" the knees during verticalization. Pain and temperature para-anesthesia from the level of L2, tactile parahypesthesia from the L3 level. Sensation of bladder feeling developed, as well as voluntary control of urination. The patient does not use catheterization or pampers. No meningeal syndrome. Functional evaluation by ASIA index: 74*98*76, level of spinal cord injury-C (incomplete). Functional evaluation by FIM index was 27%. The results of neurophysiological test showed low-amplitude, unclearly structured cerebral somatosensory evoked potentials during stimulation of both lower extremities. The amplitude of M-response from lower extremities muscles increased.

Clinical Example No. 2

Patient R-ska, age 37. Complaints: absence of voluntary movements in the legs, absence of all types of sensation from the level of inguinal fold, stool and urinary retention.

The patient suffered an injury on the thoracic level of the spinal cord in a road accident in 2005: a complicated compression fracture of ThXI and ThXII vertebrae. In early period, lower paraplegia was observed, lower para-anesthesia from the Th11 segment. Underwent 3 surgical interventions: 1. Decompressive laminectomy, transpedicular stabilization on the level of ThX-LII (November 2005, the Redeger clinic, Krakow, Poland); 2. Interbody fusion from anterio-lateral access using mesh and fixing plate on the level of ThXI-ThXII (January, 2006, the St. Tomas hospital, Tarnow, Poland); 3. Dismantling of transpedicular system and installation of rigid transpedicular stabilization at the level of ThX-LI-LII (February, 2006, the St. Tomas hospital, Tarnow, Poland). The patient repeatedly received rehabilitative treatment in reconditioning centers of Poland and Germany with no significant effect.

The patient was admitted to Neurovita Clinic on Oct. 2, 2006 to be enrolled into the research program "New Cell Technologies to Medicine". At the time of admission, the condition of the patient was compensated. Skin and visible mucosa were clean, of normal color, wet. Regional lymph nodes were not palpable. Chest regularly shaped. Breathing was independent, adequate, and free. Respiratory rate was 18 per minute. Pulse—rhythmical, of a satisfactory quality, 82 per minute. Blood pressure was 110/70. Heart tones were clear, rhythmical. The tongue was pink, wet. Abdomen was soft, painless. The liver was not enlarged, spleen was not palpable. The kidneys were not palpable in the seated position. Sense organs and endocrine glands demonstrated no rough defects. Urination was performed with the help of Foley catheter. Defecation was regular every 2 to 3 day with laxative suppositories. The consciousness was clear. The patient was time, space and personality oriented. Pupils were round, D=S, photoreaction was intact, symmetric. Ocular motility was normal, no nystagmus. No face sensation disorders. The face was symmetric, soft palate was symmetric, moving. Swallowing and phonation were intact. No atrophies, pareses, myofacsiculations of trapezius and nodding muscles. The tongue was on the median line, no atrophies, no fasciculation. Coordination tests were performed satisfactorily. Muscle tone in proximal and distal muscle groups was not changed. No hand muscle hypotrophy. Tendon and periosteal reflexes were moderate, no significant difference between the sides. Arm muscle force scores 5. Abdomen reflexes were absent. Muscle tone of leg proximal and distal muscle groups was elevated according to spastic type, 3 points by Ashworth index. Notable hypotrophy of calf muscle was observed. Tendon and periosteal reflexes were brisk, with expanded reflexogenic zones, D=S. Pathological reflexes of feet, feet and kneecap clonuses were observed. Lower spastic paraplegia. Pain and temperature paraanesthesia from the level of LI, tactile paraanesthesia from the LI level. Bowel and bladder dysfunction manifested in the stool and urine retention. No meningeal syndrome. Functional evaluation by ASIA index: 50*74*74, level of spinal cord injury-A (complete). Functional evaluation by FIM index was 31%.

The results of complex examination of the patient permitted her inclusion into the research program "New Cell Technologies—to Medicine". The patient received the course of transfusions of MASC into subarachnoid space according to the program. Received therapy led to the positive effect manifested in the sensation of bladder filling and urge for urination.

The patient underwent a surgical intervention on Mar. 7, 2007 in the NeuroVita Clinic: dismantling of transpedicular stabilizing system in ThX-LI-LII levels. LI laminectomy, meningoradiculomyelolysis, tissue engineering of the spinal cord with the application of the collagen containing heterogeneous matrix Sphero®GEL with implanted autologous ensheathing glia-olfactory cells ($3.5 \cdot 10^6$) and mobilized autologous stein cells (EC and MN). Arachnoid membrane modeling. Dura mater plasty. Stabilizing system on the level of ThX-LI-LII restored. Postsurgical period was normal, the wound healed with primary adhesion.

The patient received individual rehabilitation,

Control examination in a year after surgery demonstrated compensated condition of the patient. Skin and visible mucosa are of normal color, wet. Regional lymph nodes are not palpable. Chest is regularly shaped. Breathing is independent, adequate, and free. Respiratory rate was 16 per minute. Pulse was rhythmical, of a satisfactory quality, 86 per minute. Blood pressure was 120/80. Heart tones were clear, rhythmical. The tongue was pink, wet. Abdomen was soft, painless. The liver was not enlarged, spleen is not palpable. The kidneys were not palpable in the seated position. Sense organs and endocrine glands demonstrate no rough defects. Urination was performed with intermittent catheterization. Defecation was regular, every other day with laxative suppositories. The consciousness was clear, the patient was time, space and personality oriented. Pupils were round, D=S, photoreaction was intact, symmetric. Ocular motility was normal, no nistagmus. No face sensation disorders. The face was symmetric; soft palate was symmetric, moving. Swallowing and phonation were intact. No atrophies, pareses, myofacsiculations of trapezius and nodding muscles. The tongue was on the median line, no atrophies, no fasciculation. Coordination tests were performed satisfactorily. Muscle tone in proximal and distal muscle groups was not changed. No hand muscle hypotrophy. Tendon and periosteal reflexes were moderate, no significant difference between the sides. Arm muscle force scores 5. Abdominal reflexes are absent. Muscle tone of leg proximal and distal muscle groups was elevated according to spastic type, 1 point by Ashworth index. Moderate hypotrophy of calf muscles was observed. Tendon and periosteal reflexes were moderate, D=S. No pathological reflexes, no clonuses were observed. Movements in hip flexor muscles developed and scored 3 points, knee extensors scored 3 points, dorsal feet flexors scored 3 points, extensors of the $1^{st}$ toe-3 points, toe flexors-2 points. The patient could independently raise right leg to the height of 50 to 60 cm and make a semi-circle around the limb axis. Pain and temperature paraanesthesia from the level of L2, tactile parahypesthesia from L2 level. The sensation of a full bladder developed. No meningeal syndrome. Functional evaluation by ASIA index: 78*94*78, level of spinal cord injury-C (incomplete). Functional evaluation by FIM index was 27%. The results of a neurophysiological test showed the increase of the amplitude of activity potential of sensory fibers in lower extremities, the increase of excitation speed along sensor fibers from both sides, the increase of H-reflex habituation after stimulation from both sides.

LIST OF THE ABBREVIATIONS USED

ACBP NEPS—artificial cell-biopolymer neuroendoprosthetic system
AHSCPB—autologous hematopoietic stem cells of peripheral blood
BS-BSA—buffered saline with bovine serum albumin
CNS—central nervous system
BSC—brain or spinal cord
CSF—cerebrospinal fluid
DIT—direct immunofluorescence test
DM—dura mater
DMEM—Dulbecco's modified Eagle medium
DMSO—dimethyl sulphoxide
EC—endothelial cells
EDTA—ethylenediaminetetraacetic acid
FBS—fetal bovine serum
FGF—fibroblast growth factor
FITC—fluorescein isothyocyanate
Flt3L—haemopoietic growth factor
G-CSF—granulocyte colony-stimulating factor
GFAP—gliofibrillar protein
GLP—Good laboratory practice
HBSS—Hank's B\buffered salt solution
HEPES—4-(2-hydroxyethyl)-1-piperazineethanesulfonic acid
HSC—hematopoietic stem cells
IgG—immunoglobulin
MASC—mobilized autologous stem cells
MCA—monoclonal antibodies
MEM—minimum Eagle medium
MN—mononuclears
NC—nuclear cells
NGEC—neuroglial ensheathing cells
NGF—neural growth factor
NSC—neural stem cells
PBS—phosphate buffer saline
PE—phycoerythrin
PerCP or PCP—peridin chlorophyll
SC—spinal cord
SCF—stem cell factor
SCI—spinal cord injury
SSC—side light scattering
TPO—thrombopoetin
TLC—tube-like conductor
VNS—vegetative nervous system

What is claimed is:

1. A method of production of an implantable neuroendoprosthetic system for transubstantiation of defects of brain, spinal cord and vegetative nervous system in a mammal in reconstructive neurosurgical operations, comprising the steps of:
   providing a heterogeneous collagen-containing matrix for implantation,
   providing a cell preparation of autologous cells of a patient, and
   perfusing said preparation into said matrix to thereby obtain an elastic cell-biopolymer biologically active mass,
   wherein the cell preparation comprises placed in a NaCl solution at least one type of cells from a group comprising neural stem cells (NSC), neuroglial ensheathing cells (NGEC), endothelial cells with CD34+ marker (EC), and purified mononuclears (MN), said cells are in the following ratios (in parts according to numbers of the cells) in the cell preparation: 0.8 to 1.2 of NSC; 1.6 to 2.4 of NGEC; 4 to 6 of EC; 4000 to 6000 of MN.

2. The method of claim 1, wherein said perfusing includes centrifuging.

3. The method of claim 2, wherein said centrifuging is carried out within 1.5 to 2.5 minutes at 1500 to 2500 r/m.

4. The method of claim 1, wherein said cell preparation is prepared by defrosting cryopreserved cell products in a water bath at 37 to 40° C. with subsequent washing them at least twice in a physiological NaCl solution.

5. The method of claim 1, wherein 0.5 to 1.3% solution of NaCl is used.

6. The method of claim 1, wherein said NSC and NGEC are obtained from an olfactory sheath of the nose of a patient, and said EC and MN are obtained from either a bone marrow of the patient or a patient mobilized autologous stem cell leukoconcentrate obtained by separating patient's peripheral blood following stimulating the patient with a granulocyte colony-stimulating factor.

7. The method of claim 1, wherein said cell preparation further comprises stimulators of tissue regeneration, nerve growth factors and vascular growth factors.

8. The method of claim 1, wherein said production of said implantable neuroendoprosthetic system is carried out in sterile conditions directly in an operation room (ex tempore) or in a culture laboratory.

9. The method of claim 1, further comprising subjecting the mass to electromagnetic radiation at 1-10 GHz before implanting.

* * * * *

UNITED STATES PATENT AND TRADEMARK OFFICE
CERTIFICATE OF CORRECTION

PATENT NO. : 9,750,848 B2
APPLICATION NO. : 14/748183
DATED : September 5, 2017
INVENTOR(S) : Bryukhovetskiy et al.

Page 1 of 1

It is certified that error appears in the above-identified patent and that said Letters Patent is hereby corrected as shown below:

On the Title Page

(63) "Continuation-in-part of application No. 13/121,069, filed on Mar. 25, 2011, now abandoned, filed as application No. PCT/RU2009/000067 on Feb. 13, 2009[,now abandoned]."
Should read: "Continuation-in-part of application No. 13/121,069, filed on Mar. 25, 2011, now abandoned, filed as application No. PCT/RU2009/000067 on Feb. 13, 2009.".

Also, second column, in the section "Publications", a name is misspelled. It shows "Sykoyá et al" instead of the correct "Syková et al".

Signed and Sealed this
Seventeenth Day of October, 2017

Joseph Matal
*Performing the Functions and Duties of the*
*Under Secretary of Commerce for Intellectual Property and*
*Director of the United States Patent and Trademark Office*